US012564506B2

(12) United States Patent
Liu et al.

(10) Patent No.: US 12,564,506 B2
(45) Date of Patent: Mar. 3, 2026

(54) CHASTITY DEVICE AND METHOD OF MONITORING AND CONTROLLING THEREOF

(71) Applicant: HYTTO PTE. LTD., Singapore (SG)

(72) Inventors: Dan Liu, Guangzhou (CN); Jilin Qiu, Guangzhou (CN)

(73) Assignee: HYTTO PTE. LTD., Singapore (SG)

( * ) Notice: Subject to any disclaimer, the term of this patent is extended or adjusted under 35 U.S.C. 154(b) by 173 days.

(21) Appl. No.: 18/360,230

(22) Filed: Jul. 27, 2023

(65) Prior Publication Data

US 2025/0032293 A1 Jan. 30, 2025

(51) Int. Cl.
*A61F 5/00* (2006.01)

(52) U.S. Cl.
CPC .................................. *A61F 5/0096* (2013.01)

(58) Field of Classification Search
CPC ...... A61F 5/00; A61F 5/37; A61F 5/40; A61F 5/46; A61F 5/0096; A61F 6/02; A61F 2250/001; A61F 2005/411; A61F 2005/414; A61F 2/0004; A61F 2/0031; A61F 2/0054; A61F 6/20; A61F 6/206; A47C 15/008; A61H 19/00; A61H 19/30; A61H 19/40; A61H 19/50; A61H 2201/1628; A01K 21/00
See application file for complete search history.

(56) References Cited

U.S. PATENT DOCUMENTS

| | | |
|---|---|---|
| 5,807,299 A | 9/1998 | Mcroberts et al. |
| 6,061,840 A | 5/2000 | Alligator |
| 8,505,543 B2 | 8/2013 | Miller |
| 9,504,419 B2 | 11/2016 | Arturi |
| 11,231,085 B1 | 1/2022 | Straily |
| 2005/0223479 A1 * | 10/2005 | Griffits ...................... A41F 1/00 |
| | | 2/905 |
| 2008/0033389 A1 | 2/2008 | Bandorf et al. |
| 2008/0300452 A1 | 12/2008 | Park |
| 2011/0295156 A1 * | 12/2011 | Arturi ...................... A61N 1/22 |
| | | 600/587 |
| 2017/0119066 A1 | 5/2017 | Robinson |
| 2017/0290530 A1 | 10/2017 | Hong et al. |

(Continued)

FOREIGN PATENT DOCUMENTS

| | | | | |
|---|---|---|---|---|
| KR | 20080000910 A | * | 1/2008 | ............... A61F 5/37 |
| WO | 2024215331 A1 | | 10/2024 | |

OTHER PUBLICATIONS

Machine Translation of Publication No. KR-20080000910A created from espacenet.com on Jul. 7, 2025 (Year: 2008).*

(Continued)

*Primary Examiner* — Alireza Nia
*Assistant Examiner* — Gina McCarthy
(74) *Attorney, Agent, or Firm* — Holtz, Holtz & Volek PC

(57) ABSTRACT

Embodiments of the present disclosure disclose a method of monitoring and controlling a chastity device. The method includes generating, by an electronic controller, a report signal indicative of a change in a wearing state of the chastity device. Further, the method includes transmitting, by the electronic controller, the report signal to a monitor client device associated with a monitor. The report signal is generated by the electronic controller in response to an input signal received from a peripheral device installed with the chastity device.

15 Claims, 10 Drawing Sheets

(56)           References Cited

U.S. PATENT DOCUMENTS

2022/0400646 A1    12/2022  Eversole
2023/0346631 A1 *  11/2023  Siles ...................... A61H 19/32

OTHER PUBLICATIONS

Techno-Physical Feminism: Anti-Rape Technology, Gender, and Corporeal Surveillance, Renee Marie Shelby, Sep. 9, 2019 pp. 2-4, United States of America.
Office Action (Non-Final Rejection) dated Oct. 23, 2025, issued in related U.S. Appl. No. 18/497,894.

* cited by examiner

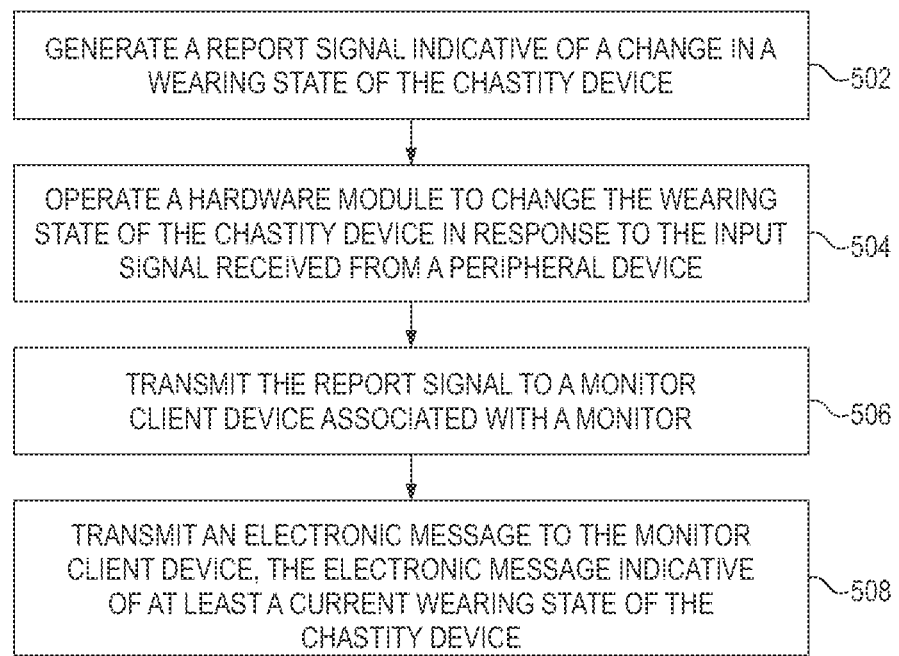

GENERATE A REPORT SIGNAL INDICATIVE OF A CHANGE IN A WEARING STATE OF THE CHASTITY DEVICE ~502

OPERATE A HARDWARE MODULE TO CHANGE THE WEARING STATE OF THE CHASTITY DEVICE IN RESPONSE TO THE INPUT SIGNAL RECEIVED FROM A PERIPHERAL DEVICE ~504

TRANSMIT THE REPORT SIGNAL TO A MONITOR CLIENT DEVICE ASSOCIATED WITH A MONITOR ~506

TRANSMIT AN ELECTRONIC MESSAGE TO THE MONITOR CLIENT DEVICE, THE ELECTRONIC MESSAGE INDICATIVE OF AT LEAST A CURRENT WEARING STATE OF THE CHASTITY DEVICE ~508

FIG. 5

CHASTITY DEVICE AND METHOD OF MONITORING AND CONTROLLING THEREOF

TECHNICAL FIELD

The present disclosure relates to a chastity device, and more particularly relates to a method of monitoring and controlling the chastity device in an emergency.

BACKGROUND

A chastity device is used to prevent a wearer from engaging in certain types of sexual activity without the permission of a monitor. The wearer (male or female) may wear the chastity device in several instances. In one instance, the chastity device may be worn by the wearer for not having sex with anyone. In another instance, the chastity device may be worn by the wearer for having sex only with a pre-defined person (e.g., a husband or a wife).

Typically, the chastity device is provided with a locking/unlocking mechanism. The locking/unlocking mechanism may be operated mechanically or electronically. If the chastity device is provided with a mechanically operated locking/unlocking mechanism, a key used for locking/unlocking purposes is often held by the monitor. The monitor may lock/unlock the chastity device through the key, based on mutually agreed discipline between the wearer and the monitor. However, there are chances that the key being used to lock/unlock the chastity device may get misplaced during an emergency. Specifically, due to misplacing of the key by the monitor, the emergency unlocking of the wearer's chastity device is difficult, and therefore, forceful unlocking of the chastity device is needed in the emergency.

Further, the locking/unlocking mechanism of some of the chastity devices is designed in a manner that the locking/unlocking can be operated electronically through a remote-control application. Such a locking/unlocking mechanism of the chastity device is communicably (e.g., wirelessly) operated by a suitable electronic device of the monitor (e.g., a smartphone). The electronic device cases the locking/unlocking functionally of the chastity device compared to the above-discussed physically operated locking/unlocking mechanism. However, the electronic device configured to operate the locking/unlocking functionality of the chastity device also has some limitations. For example, the electronic device of the monitor can only be operated in a predefined operating range of the chastity device and may get disabled beyond the operating range. Therefore, the electronic device of the monitor has to be operated within the operating range of the chastity device. Also, there is a chance that the electronic device may run out of electrical power on some occasions and thus, may face an operating issue in an emergency. As a result, a forceful unlocking of the chastity device would be needed. However, the forceful unlocking of the chastity device in an emergency involves a risk of injury to the wearer and/or damage to the chastity device.

Therefore, there exists a need to develop a structural mechanism and a method of monitoring and controlling the chastity device in a manner that does not suffer from the aforementioned deficiencies.

SUMMARY

Various embodiments of the present disclosure disclose a chastity device and provide a method of monitoring and controlling the chastity device in an emergency.

According to a first aspect of the present disclosure, there is provided a method of monitoring and controlling a chastity device. The method includes generating, by an electronic controller, a report signal indicative of a change in a wearing state of the chastity device. Also, the method includes transmitting, by the electronic controller, the report signal to a monitor client device associated with a monitor. The report signal is generated by the electronic controller in response to an input signal received from a peripheral device associated with the chastity device.

In one aspect, the peripheral device is selected from a group including input devices, a communication interface, and a sensing module.

In one aspect, the method further includes generating, by the sensing module, the input signal in response to physiological characteristics of a wearer of the chastity device.

In one aspect, the method further includes operating, by the electronic controller, a hardware module to change the wearing state of the chastity device in response to the input signal received from the peripheral device.

In one aspect, the method further includes determining, by the sensing module, a tension in a belt of the hardware module, transmitting, by the sensing module, tension information to the electronic controller as a part of the input signal, and controlling, by the electronic controller, the tension in the belt to unlock the chastity device. The report signal reports the unlocking of the chastity device to the monitor client device.

In one aspect, the monitor client device associated with the monitor is communicably coupled to the hardware module and is adapted to provide a control signal to the electronic controller for change in the wearing state of the chastity device.

In one aspect, the hardware module includes a first lock switch and a second lock switch. The first lock switch is configured to control the wearing state of the chastity device and the second lock switch is configured to control a urination port opening of the chastity device.

In one aspect, a wearer client device associated with the wearer of the chastity device is communicably coupled to the hardware module and is authorized to provide the control signal to the electronic controller for change in the wearing state of the chastity device, after receiving an authorization signal from the monitor client device.

In one aspect, the method further includes determining, by the electronic controller, whether preset operating parameters of the hardware module matches reported operating parameters reported by the peripheral device, wherein the reported operated parameters are included in the input signal, and operating, by the electronic controller, the hardware module upon matching the preset operating parameters of the hardware module with the reported operating parameters reported by the peripheral device.

In one aspect, the reported operating parameters include one of a power parameter and a time parameter.

In one aspect, the reported operating parameters of the hardware module include communication network parameters and the peripheral device is a communication interface.

In one aspect, the reported operating parameters include information associated with a second hardware module of a second chastity device.

In one aspect, the change in the wearing state of the chastity device includes locking or unlocking of the chastity device in response to a control signal received from the monitor client device or the wearer client device, the report signal reporting the locking or the unlocking to the monitor client device.

In one aspect, the method further includes transmitting, by the electronic controller, an electronic message to the monitor client device, the electronic message indicative of at least a current wearing state of the chastity device.

In one aspect, the method further includes transmitting, by the electronic controller, the electronic message to a storage module and a wearer client device associated with the wearer, wherein the storage module records the electronic message.

According to another aspect of the present invention, there is provided a chastity device. The chastity device includes a peripheral device, an electronic controller, and a memory unit operably connected to the electronic controller. The memory unit includes machine-readable instructions, that when executed by the electronic controller, enable the electronic controller to generate a report signal indicative of a change in a wearing state of the chastity device, in response to an input signal received from the peripheral device installed with the chastity device, and transmit the report signal to a monitor client device associated with a monitor.

In one aspect, the peripheral device is selected from a group including input devices, a communication interface, and a sensing module.

In one aspect, the chastity device further includes a hardware module and the peripheral device includes a sensing module, the electronic controller further enabled to operate the hardware module to change the wearing state of the chastity device in response to the input signal received from the peripheral device, the sensing module configured to determine a tension in a belt of the hardware module, and transmit the tension information to the electronic controller as a part of the input signal, the electronic controller being further enabled to control the tension in the belt to unlock the chastity device. The report signal reports the unlocking of the chastity device to the monitor client device.

In one aspect, the hardware module includes a first lock switch and a second lock switch, the first lock switch is configured to control the wearing state of the chastity device, and the second lock switch is configured to control a urination port opening of the chastity device.

In one aspect, the electronic controller is further enabled to determine whether preset operating parameters of the hardware module matches reported operating parameters reported by the peripheral device, the reported operated parameters are included in the input signal, and operate the hardware module upon matching the preset operating parameters of the hardware module with the reported operating parameters reported by the peripheral device.

In one aspect, the chastity device further includes a storage module. The electronic controller is further enabled to transmit the electronic message to the storage module and a wearer client device associated with the wearer. The storage module is configured to record the electronic message.

BRIEF DESCRIPTION OF THE DRAWINGS

The following detailed description of illustrative embodiments is better understood when read in conjunction with the appended drawings. To illustrate the present disclosure, exemplary constructions of the disclosure are shown in the drawings. However, the present disclosure is not limited to a specific device, or a tool and instrumentalities disclosed herein. Moreover, those in the art will understand that the drawings are not to scale.

FIG. 5 is a flow diagram illustrating a method for monitoring and controlling the chastity device, in accordance with an embodiment of the present disclosure.

Figure 1A:
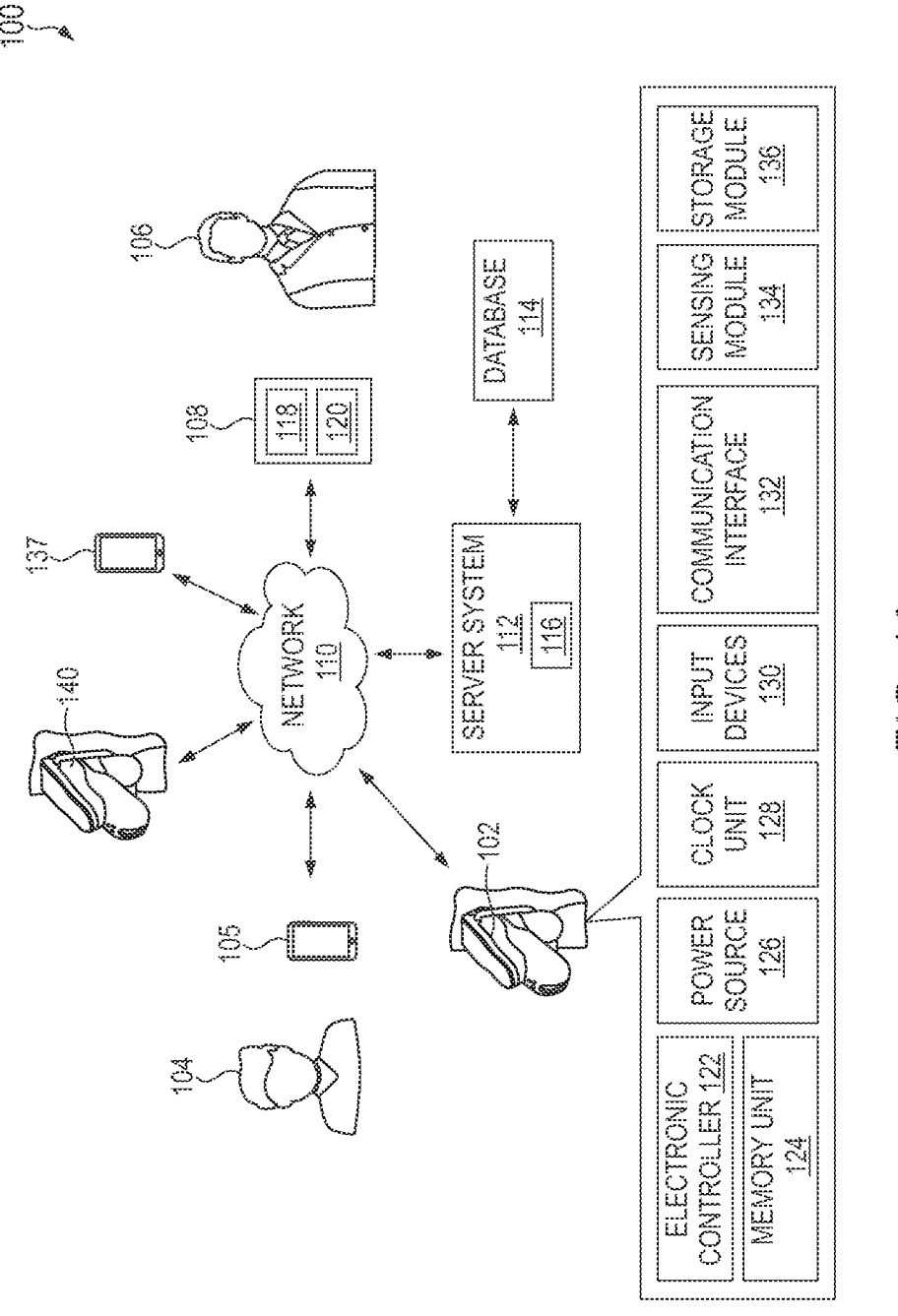
FIG. 1A is an example representation of an environment related to at least some examples of the present disclosure.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Embodiments of the present disclosure provide a chastity device to be worn by a wearer and a method of monitoring and controlling the chastity device. The chastity device includes an electronic controller that detects/changes a wearing state of the chastity device on receiving an input signal from a peripheral device. The peripheral device may be selected from a group consisting of input devices, a communication interface, and a sensing module. On changing the wearing state of the chastity device, the electronic controller generates a report signal indicating the change in the wearing state and transmits the report signal to a monitor client device associated with a monitor. For example, the sensing module may generate the input signal in response to physiological characteristics of the wearer. The physiological characteristics may include, for example, a size of the genitals, a presence of an injury near the groin area, or some other physical ailment. The sensing module may also determine other parameters such as a tension value of the tension in a belt of the chastity device and include the tension value in the input signal.

Alternately, the communication interface may generate the input signal on receipt of a control signal from the monitor client device or a wearer client device associated with the wearer. In that regard, the wearer client device may be able to generate and transmit the control signal to the electronic controller only after receiving an authorization signal from the monitor client device. In another scenario, the input devices may include lock switches, such as a first lock switch and a second lock switch, and the input devices may generate the input signal on the actuation of one or more of the first lock switch and the second lock switch.

In response to the receipt of the input signal, the electronic controller may then operate a hardware module of the chastity device to change the wearing state of the chastity device. In that regard, before operating the hardware module, the electronic controller may perform several verification steps. For example, the electronic controller may compare reported operating parameters included in the input signal with preset input parameters associated with the hardware module. The reported operating parameters may include power parameters such as a State of Charge (SoC) of a battery of the chastity device, a time parameter such as a duration elapsed since the chastity device was last engaged, and a network parameter such as a Service Set Identifier (SSID) of a network to which the chastity device may be connected. The reported operating parameters may also include information associated with a second hardware module of a second chastity device. The associated information may include a distance of the second chastity device from the hardware module, network parameters, power parameters, and time parameters of the second chastity device.

In that regard, the report signal may report the locking and unlocking of the chastity device and may be accompanied by an electronic message. The electronic message may include details of a current wearing state of the chastity device. Further, the electronic message may also include a wearing state change time instance information, the wearing state of the chastity device before and after the instance of the wearing state change, the mode of change of the wearing state, etc. In addition to getting delivered to the monitor client device, the electronic message is also stored in a storage device.

Various example embodiments of the present disclosure are described hereinafter with reference to FIG. 1 to FIG. 5.

FIG. 1A is an example representation of an environment 100 related to at least some examples of the present disclosure. The environment 100 includes a chastity device 102 designed to be worn by a wearer 104. The chastity device 102 includes a plurality of mechanical and electronic components that prevents the sexual activities of the wearer 104. More specifically, the chastity device 102 worn by the wearer 104 is configured to constrain the wearer 104 from engaging in certain types of sexual activities or having erotic thoughts without a permission of a monitor 106. In the illustrated embodiment, the wearer 104 of the chastity device 102 is a boy and the monitor 106 monitoring and controlling the chastity device 102 is a man who may be a guardian of the boy or the wearer 104. The guardian (i.e., the monitor 106) restricts the boy or the wearer 104 from engaging in sexual activities (e.g., intercourse, masturbation, etc.) by means of the chastity device 102.

Figure 1B:
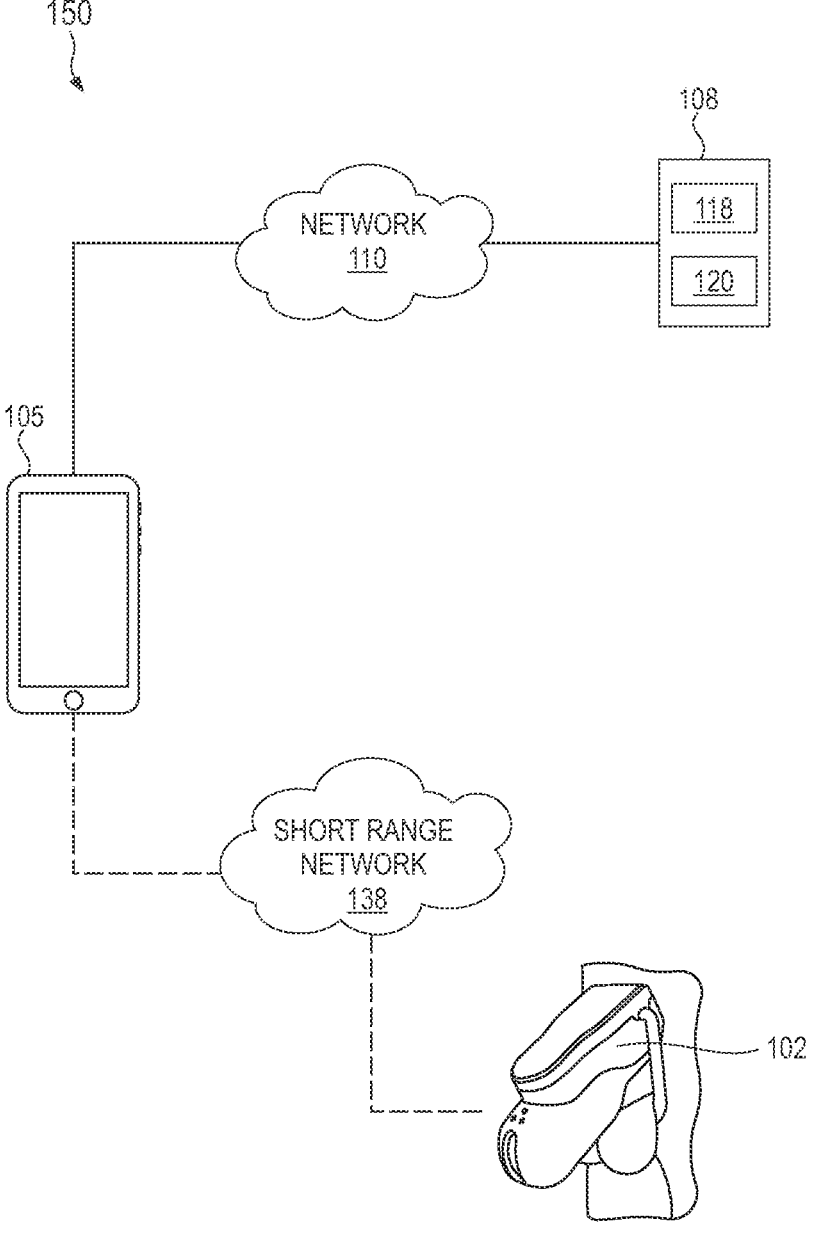
FIG. 1B illustrates an alternative connection arrangement between a chastity device, a wearer client device, and a monitor client device, in accordance with an embodiment of the present disclosure.

In the illustrated embodiment, the monitor 106 remotely controls and operates the chastity device 102, by providing an electronic input using a monitor client device 108. As shown, the chastity device 102 and the monitor client device 108 are connected with each other via a network 110. The network 110 may include at least one of a Local Area Network (LAN), a Wide Area Network (WAN), a Light Fidelity (Li-Fi) network, a Metropolitan Area Network (MAN), a fiber-optic network, a coaxial cable network, an internet, a satellite network, an Infrared (IR) network, a Radio Frequency (RF) network, a virtual network, or any combination thereof. FIG. 1B illustrates an alternative connection arrangement 150 between the chastity device 102, the wearer client device 105, and the monitor client device 108, in accordance with an embodiment of the present disclosure. The chastity device 102 may be connected with the monitor client device 108 through the wearer client device 105. In that regard, the chastity device 102 may be connected with the wearer client device 105 through a short-range network 138, such as Bluetooth or Near Field Communication (NFC) and exchange messages with the wearer client device 105 through the short-range network 138. Further, the wearer client device 105 may further connect to the monitor client device 108 through the network 110. In that regard, the wearer client device 105 may act as an intermediary between the chastity device 102 and the monitor client device 108.

The electronic input provided by the monitor 106 through the monitor client device 108 may include but is not limited to, enabling or disabling the operation of the plurality of mechanical and electronic components of the chastity device 102. In a non-limiting example, the monitor 106 may use an interactive standalone application acting as a client software and enabled in the monitor client device 108 to provide the electronic input to the chastity device 102 through the network 110. The monitor client device 108 adapted to be operated by the monitor 106 may be any electronic device such as, but not limited to, a smartphone, a laptop, a tablet device, a Personal Computer (PC), a Personal Digital Assistance (PDA), and wearable devices. In the illustrated configuration, the monitor client device 108 is the smartphone that includes the plurality of standalone applications developed to monitor and control the operation of the chastity device 102 worn by the wearer 104 by providing the electronic input to the chastity device 102 via the network 110. In an embodiment, when the chastity device 102 worn by the wearer 104 comes in contact with a pre-defined network area (e.g., home, office, etc.), the electronic controller 122 generates an input signal. Further, the electronic controller 122 transmits the generated input signal to the monitor client device 108, indicating that the chastity device 102 worn by the wearer 104 comes in contact with the pre-defined network area.

In one embodiment, when the chastity device 102 is connected to the monitor client device 108, a message is sent from the chastity device 102 to the monitor client device 108. The same message may then be transmitted from the wearer client device 105 to the monitor client device 108. Alternately, the wearer client device 105 may generate a new message in response to the message received from the chastity device 102 or otherwise and transmit the new message to the monitor client device 108. The message sent to the monitor client device 108 contains information, such as network identity (ID), Internet protocol (IP) address, public encryption key, etc. about the chastity device 102. Alternatively, the chastity device 102 sends the message directly to the monitor client device 108 when the preset conditions are met. The preset conditions may include the monitor client device 108 having a unique registration ID, IP address, or public encryption key and encrypted handshake message that the chastity device 102 may utilize to validate the monitor client device 108. In addition to other constructional features that will be discussed in the following discussion, the chastity device 102 further includes an electronic controller 122, a memory unit 124, a communication interface 132, and a sensing module 134. As an example, the electronic controller 122 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU). a hardware accelerator, a special-purpose computer chip, integrated circuits, or the like.

The memory unit 124 may be a volatile storage memory, such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc. The chastity device 102 may also include a storage module 136. The storage module 136 may be a non-volatile storage memory such as EPROM, EEPROM, flash memory or the like. The memory unit 124 includes machine-readable instructions for execution by the electronic controller 122 for controlling the operation of the chastity device 102. The communication interface 132 may be a device or a module enabling direct connectivity via wires and connectors such as USB, HDMI, VGA, or wireless connectivity such as Bluetooth or Wi-Fi or Local Area Network (LAN) or Wide Area Network (WAN) implemented through TCP/IP, IEEE 802.x. GSM, CDMA, LTE, or other equivalent protocols. The sensing module 134 may include several sensors for sensing a state of the chastity device 102. For example, the sensing module 134 may include one or more sensors for sensing tension in a belt of the chastity device 102, determining if the chastity device 102 is engaged or disengaged. Further, the sensing module 134 may also include a voltage sensor such as a potentiometer to measure voltage in an internal circuitry of the chastity device 102. Other sensors that may form a part of the sensing module 134 may include pressure sensors, proximity sensors, optical sensors, etc.

Further, the illustrated embodiment of the environment 100 includes a server system 112 and a database 114. The server system 112 may be deployed as a standalone server or can be implemented in the cloud as Software as a Service (Saas). The server system 112 provides or hosts an application 116 for, inter alia, managing unique code generation and enabling and validating user reviews. Furthermore, the monitor client device 108 includes a client processor 118 and a client memory unit 120. The client memory unit 120 is operably connected to the client processor 118. The client memory unit 120 includes machine-readable instructions that when executed by the client processor 118, enable the client processor 118 to, inter alia, provide a control signal to the electronic controller 122 for change in the wearing state of the chastity device 102.

Figure 2:
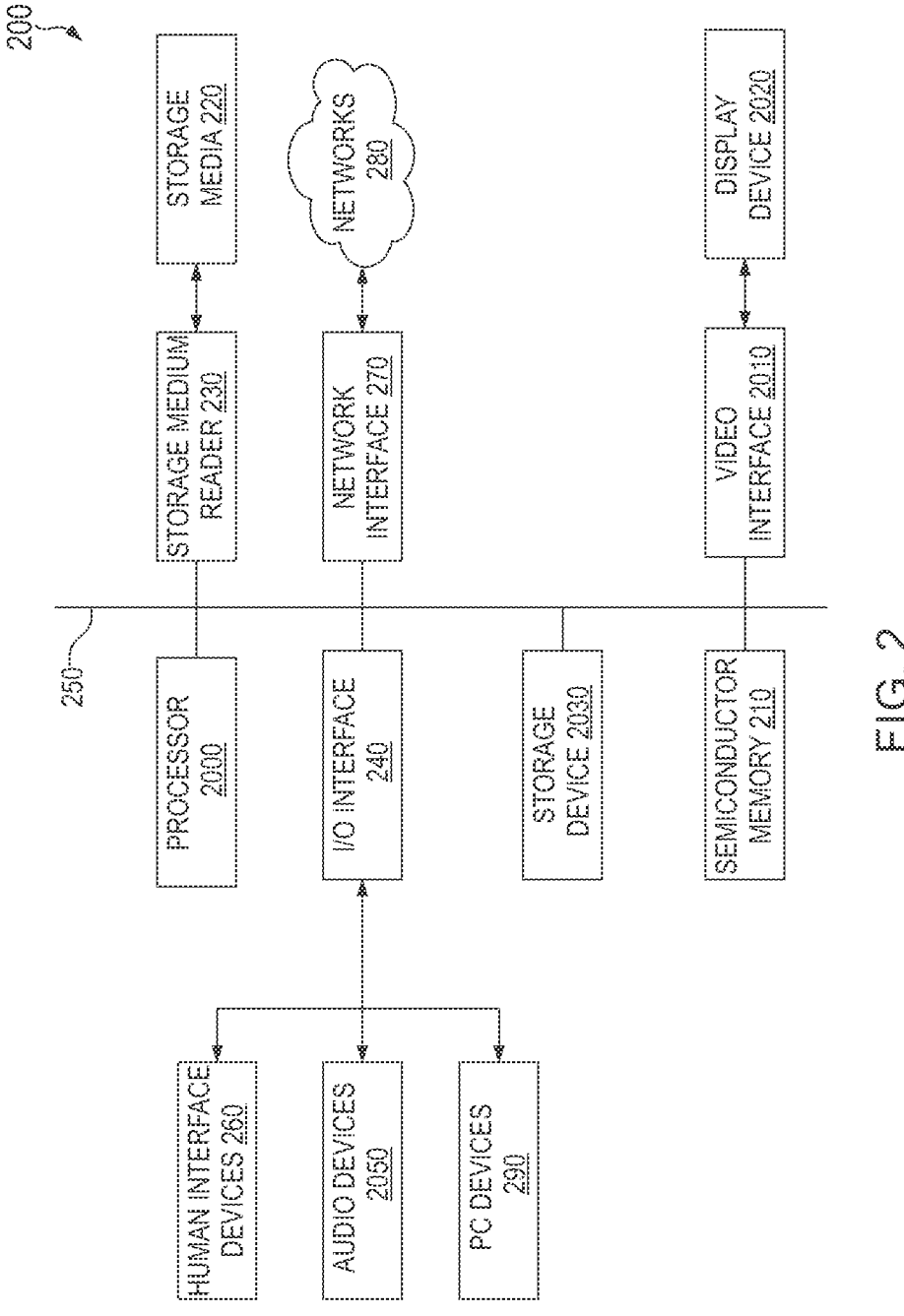
FIG. 2 is a block diagram of a computing device, in accordance with an embodiment of the present disclosure.

FIG. 2 is a block diagram of a computing device 200, in accordance with an embodiment of the present disclosure. In an embodiment, the computing device 200 takes the form of the server system 112 described in FIG. 1. In this manner, the computing device 200 is adapted to include functionality for communication with the network 110, storage capability (such as the database 114) for storing the data exchanged between the chastity device 102 and the monitor client device 108.

However, it should be noted that the monitor client device 108 of the monitor 106 may also be depicted as the computing device 200. In this manner, the computing device 200 may include differing technical integers, such as a display device 2020 electronically connected to a video interface 2010, one or more human interface devices 260, and the like. In other words, the technical integers of the computing device 200 shown in FIG. 2 are examples only, and variations, adaptations and the like may be made thereto within the purposive scope of the embodiments described herein and having regard for the particular application of the computing device 200.

In particular, the steps of methods for monitoring and controlling the chastity device 102, as described in further detail below, may be implemented as computer program code instructions executable by the computing device 200. The computer program code instructions are executable by the computing device 200. The computer program code may be formed in the form of instruction libraries, such as dynamic link libraries (DLL), wherein each of the libraries performs one or more steps of the methods as would be discussed in the following discussion. Additionally, a subset of one or more libraries may perform graphical user interface tasks relating to the steps of the methods.

The computing device 200 further includes a semiconductor memory 210 including volatile memory such as Random Access Memory (RAM) or Read Only Memory (ROM). The semiconductor memory 210 may include either RAM or ROM or a combination of RAM and ROM. Furthermore, the computing device 200 includes a computer program code storage medium reader 230 for reading the computer program code instructions from computer program code storage media 220. The storage media 220 may be optical media such as CD-ROM disks, magnetic media such as floppy disks and tape cassettes, or flash media such as SUB memory sticks.

Moreover, the computing device 200 includes an I/O interface 240 for communicating with one or more peripheral devices (not shown in FIG. 2). The I/O interface 240 may offer both serial and parallel interface connectivity. For example, the I/O interface 240 may include a Small Computer System Interface (SCSI), and Universal Serial Bus (USB). The I/O interface 240 may also communicate with one or more human interface devices 260 such as keyboards, pointing devices, such as Recommended Standard 232 (RD-2332) interface, for interfacing the computing device 200 with one or more personal computer (PC) devices 290. The I/O interface 240 may also include an audio interface for communicating audio signals to one or more audio devices 2050, such as a speaker or a buzzer.

The computing device 200 also includes a network interface 270 for communicating with one or more computer networks 280, such as the network 110. Computer program code instructions may be loaded into the storage device 2030 from the storage media 220 using the storage medium reader 230 or from the network 110 using the network interface 270. During the bootstrap phase, an operating system and one or more software applications are loaded from the storage device 2030 into the semiconductor memory 210. During the fetch-decode-execute cycle, a processor 2000 fetches computer program code instructions from the semiconductor memory 210, decodes the instructions into machine code, executes the instructions, and stores one or more intermediate results in the semiconductor memory 210.

In this manner, the instructions stored in the semiconductor memory 210, when retrieved and executed by the processor 2000, may configure the computing device 200 as a special-purpose machine that may perform the functions described above. The computing device 200 also includes a communication bus subsystem 250 for interconnecting the various devices described above. The communication bus subsystem 250 may offer parallel connectivity such as Industry Standard Architecture (ISA) conventional Peripheral Component Interconnect (PCI) and the like or serial connectivity such as PCI Express (PCIe), Serial Advanced Technology Attachment (Serial ATA), and the like.

Figure 3A:
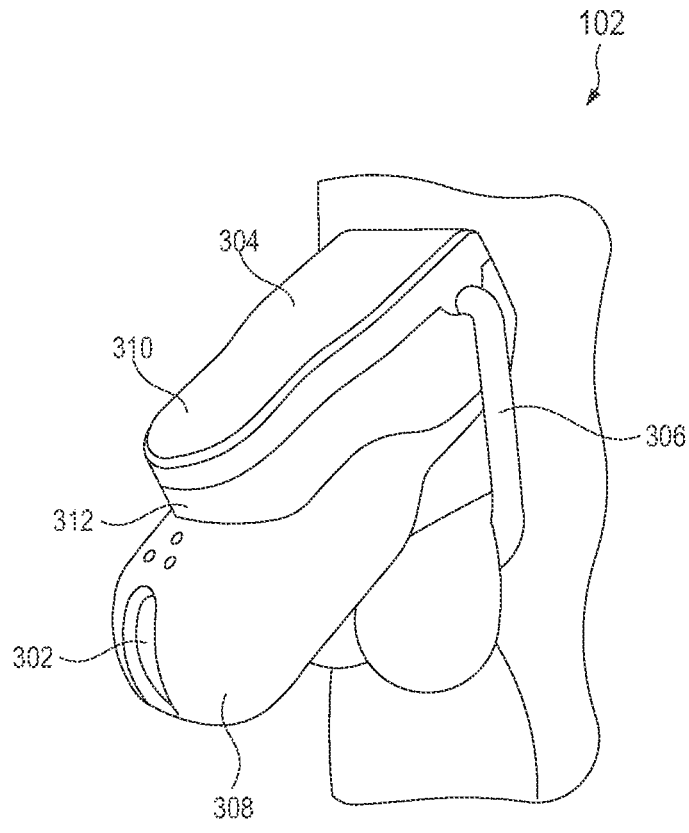
FIG. 3A illustrates a perspective view of a chastity device worn by a wearer, in accordance with an embodiment of the present disclosure.
Figure 3B:
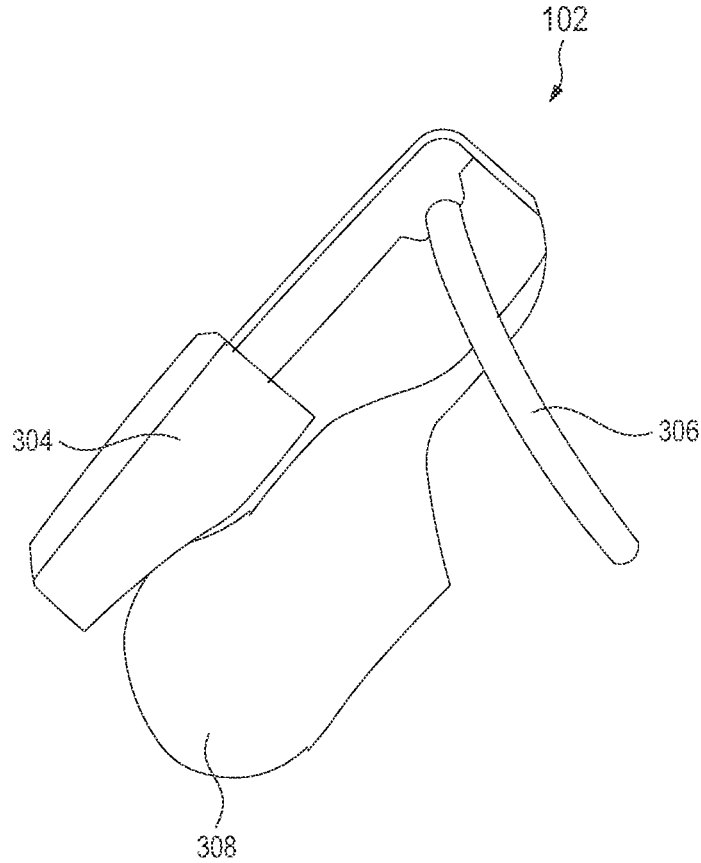
FIG. 3B illustrates a side view of the chastity device of FIG. 3A, in accordance with an embodiment of the present disclosure.

FIG. 3A illustrates a perspective view of the chastity device 102 worn by the wearer 104, in accordance with an embodiment of the present disclosure. FIG. 3B illustrates a side view of the chastity device 102 of FIG. 3A, in accordance with an embodiment of the present disclosure. As shown, the chastity device 102 is designed to secure a penis 302 (see FIG. 3A) of the wearer 104, thereby preventing the wearer 104 from engaging in certain types of sexual behavior without the permission of the monitor 106. The chastity device 102 includes a covering member 304, a belt 306, and a capped tube 308. The covering member 304 is configured to cover the plurality of mechanical and electronic components disposed within the chastity device 102. The plurality of mechanical and electronic components of the chastity device 102 are illustrated and discussed in further detail with respect to FIG. 4A and FIG. 4B in the following discussion. In an embodiment, the covering member 304 is constructed in a manner to be split at least in two parts. The split parts (i.e., a top part 310 and a bottom part 312) may be assembled through suitable fastening elements. In a non-limiting example, the glue may be applied on the border of contacting surfaces of the top part 310 and the bottom part 312 designed to form the covering member 304. It should be noted that the shape of the covering member 304 is not limited to that shown in FIG. 1, and can take other forms and shapes, based on the design configuration of the chastity device 102.

Further, as shown, the belt 306 of the chastity device 102 is seated around the base of the penis 302, from under the testicles of the wearer 104. The belt 306 used herein is a flexible member that has been designed to eliminate chances of sliding or detachment of the chastity device 102 without the permission of the monitor 106. The belt 306 may be made up of a suitable soft material (e.g., rubber or leather) that would eliminate the chances of causing injury to the penis 302 of the wearer 104.

Furthermore, the capped tube 308 is designed to secure the penis 302 of the wearer 104. More specifically, the capped tube 308 of the chastity device 102 is designed to secure the penis 302 of the wearer 104 in a flaccid state. It should be noted that the size of the capped tube 308 may not be limited to one particular value and may be of any size, depending upon the size of the penis 302 of the wearer 104. The capped tube 308 may be made up of a suitable lightweight material but rigid material that does not cause injury or infection to the penis 302 of the wearer 104. For example, lightweight but rigid materials such as silicon, borosilicate glass, Lucite, stainless steel, etc., can be used to fabricate the capped tube 308 of the chastity device 102. The geometrical configuration of the capped tube 308 is such that the attachment and detachment capability of the capped tube 308 provides case of cleaning the chastity device 102. The case of cleaning of the capped tube 308 would assist in maintaining a specific hygiene level in the chastity device 102.

Figure 3C:
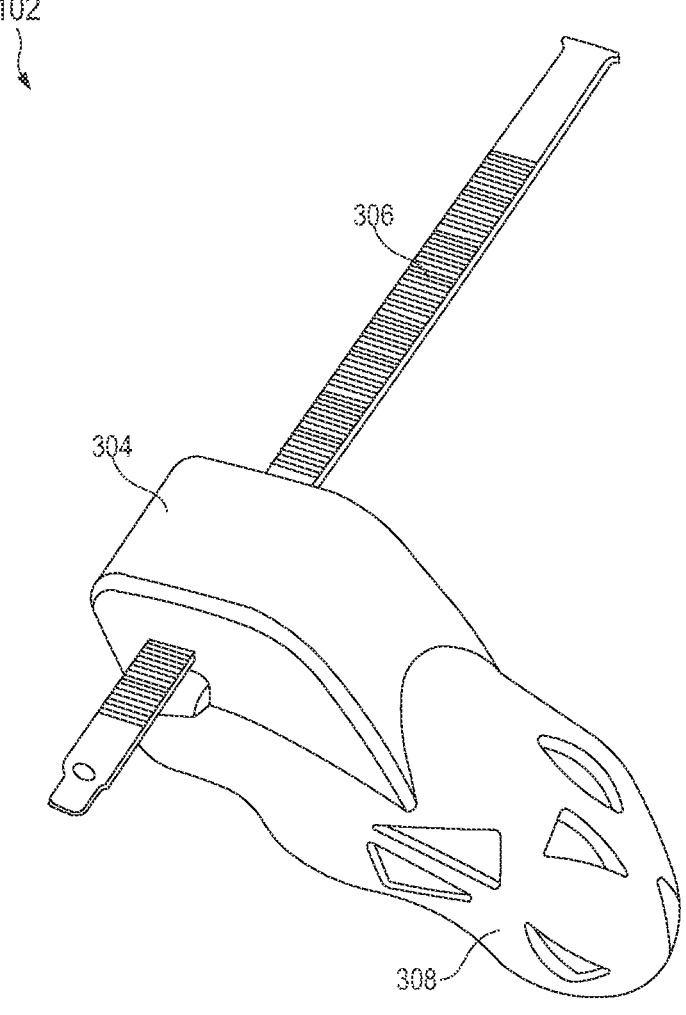
FIG. 3C illustrates a perspective view of the chastity device in an unlocked state of the belt, in accordance with an embodiment of the present disclosure.
Figure 3D:
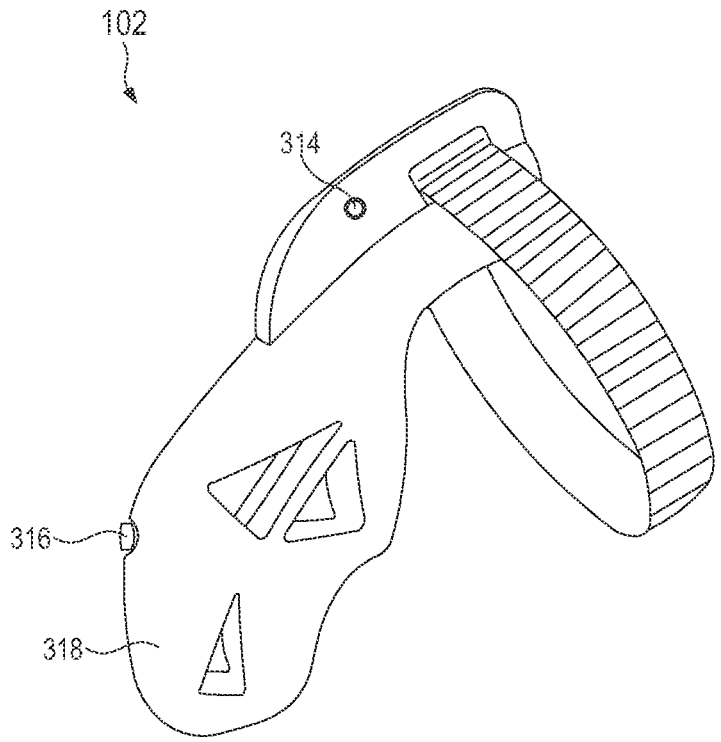
FIG. 3D illustrates a side view of the chastity device in a lock state of the belt, in accordance with an embodiment of the present disclosure.

FIG. 3C illustrates a perspective view of the chastity device 102 in an unlocked state of the belt 306, in accordance with an embodiment of the present disclosure. FIG. 3D illustrates a side view of the chastity device 102 in a locked state of the belt 306, in accordance with an embodiment of the present disclosure. In an embodiment, the belt 306 can be pulled in one direction for tightening. The tightening creates locking of the chastity device 102. In contrast, the belt 306 can also be pulled in the opposite direction for loosening. The loosening creates unlocking of the chastity device 102. The chastity device 102 also includes a first lock switch 314 and a second lock switch 316 (see FIG. 3D). In the illustrated embodiment, the first lock switch 314 is configured to control the wearing state of the chastity device 102, and the second lock switch 316 is configured to control a urination port opening 318 of the chastity device 102. In that manner, the first lock switch 314 and the second lock switch 316 may act as input devices 130 (See FIG. 1) of the chastity device 102.

In an embodiment, the belt 306 adjusts a tightness of the chastity device 102. When unlocking operation on the belt 306 of the chastity device 102 is detected, the corresponding unlocking information for the operation is generated. The unlocking operation causes the belt 306 of the chastity device 102 to switch from the locked state to the unlocked state. The sensing module 134 (e.g., tension load cell) first measures the tightness level of the belt 306 of the chastity device 102, then the sensing module 134 generates an image and/or information that represents the tightness level of the belt 306 of the chastity device 102 and sends the image and/or information to the monitor client device 108 over the network 110. The image and/or information may also be stored in the database 114 through the server system 112 for later reference and/or system improvements.

Figure 4A:
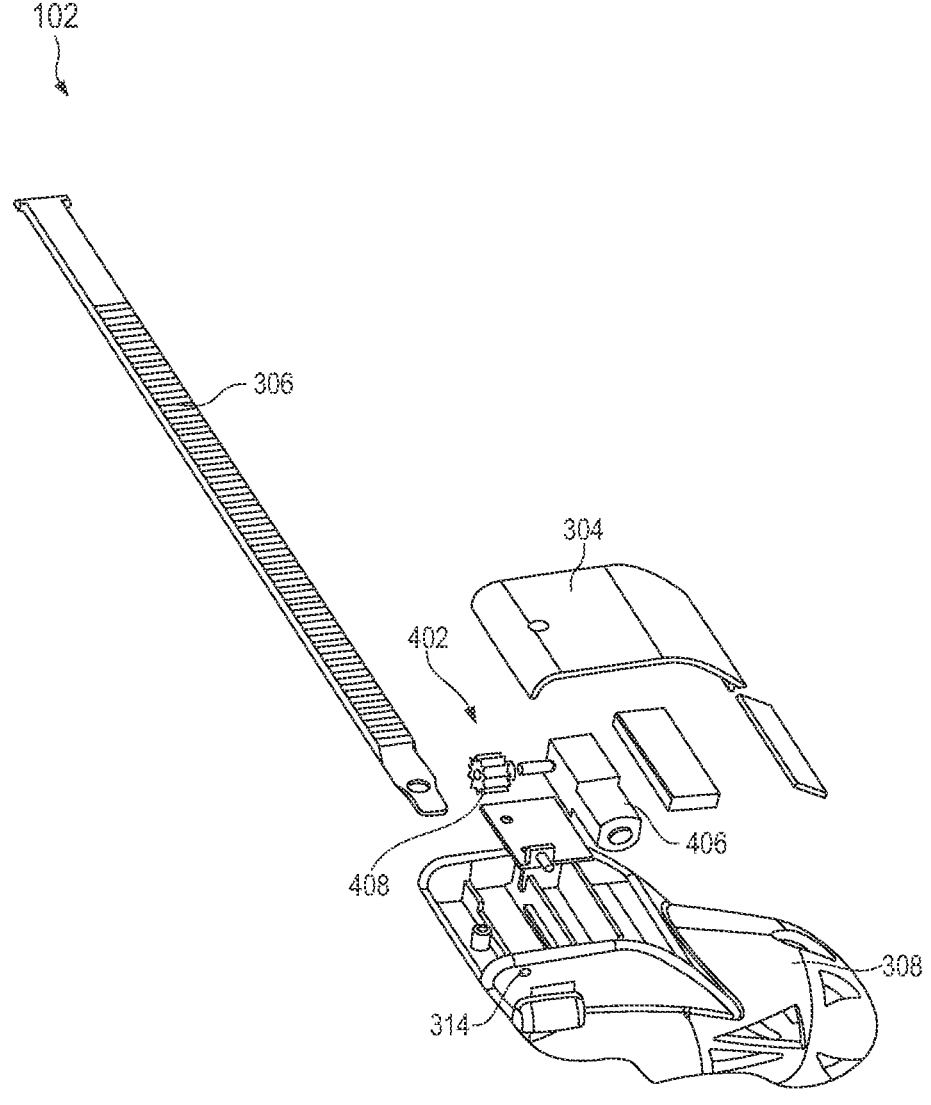
FIG. 4A illustrates an exploded view of the chastity device of FIG. 3C, in accordance with one embodiment of the present disclosure.

FIG. 4A illustrates an exploded view of the chastity device 102 of FIG. 3C, in accordance with one embodiment of the present disclosure. In the illustrated embodiment, the chastity device 102 has been illustrated to include a hardware module 402. The hardware module 402 includes a motor 406, a transmission gear 408, and the first lock switch 314. The monitor client device 108 associated with the monitor 106 is communicably coupled to the hardware module 402. The monitor client device 108 is adapted to provide the control signal to the electronic controller 122 for change in the wearing state of the chastity device 102. The motor 406, the transmission gear 408, and the first lock switch 314 are configured at least to operate the belt 306 for tightening and loosening purposes. Tightening of the belt 306 is required to lock the chastity device 102 and loosening of the belt 306 is required to unlock the chastity device 102.

Figure 4B:
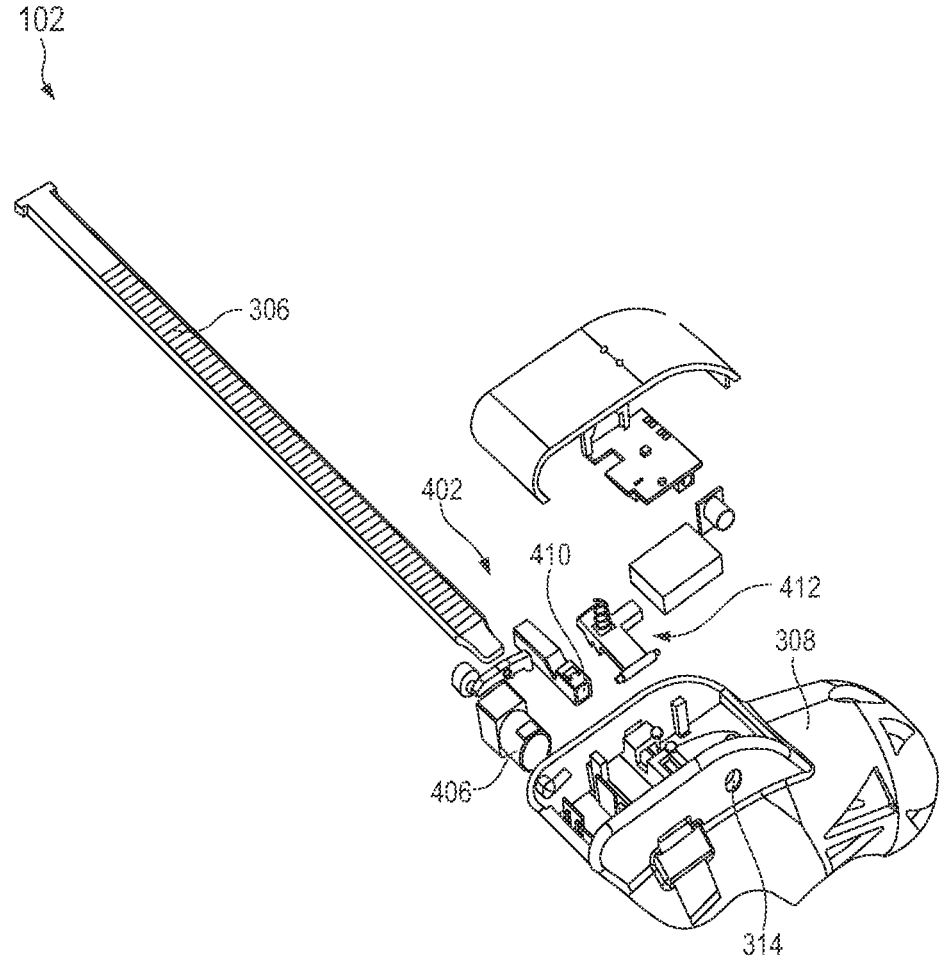
FIG. 4B illustrates an exploded view of the chastity device of FIG. 3C, in accordance with another embodiment of the present disclosure.

FIG. 4B illustrates an exploded view of the chastity device 102 of FIG. 3C, in accordance with another embodiment of the present disclosure. The chastity device 102 of FIG. 4B does not include the motor 406 or the transmission gear 408 for the operation of the belt 306. Instead, the belt 306 is configured to be manually tightened and locked in a desired position using a manual lock 412. The manual lock 412 may be disengaged for further adjustment of the belt 306 through a manual lock switch 410 provided with the hardware module 406. However, the sensing module 134 may still be able to sense the tension in the belt 306 irrespective of whether the belt 306 is operated through the motor 406 and the transmission gear 408, or operated manually and held in place using the manual lock 412.

In one embodiment, when the wearer 104 presses the manual lock switch 410, the manual lock 412 may get disengaged from the belt 306. As a result, the belt 306 gets loosened, and accordingly, unlocking of the chastity device 102 takes place. The sensing module 134 senses a decrease in the tension of the belt 306 and transmits the sensed data to the electronic controller 122 as a part of the input signal. Based on the input signal, the controller 122 first generates the report signal and then sends the generated report signal to the monitor client device 108. Therefore, the act of pressing of the manual lock switch 410 performed by the wearer 104 generates the report signal and the generated report signal is sent to the monitor client device 108.

In another embodiment, the belt 306 can be tightened or loosened without pressing the manual lock switch 410. The monitor client device 108 may send the control signal to the electronic controller 122. Further, the electronic controller 122 may process the control signal and operate the hardware module 406. In that regard, the belt 306 may be tightened or loosened without pressing the manual lock switch 410.

In addition to the electronic controller 122 and the memory unit 124, the chastity device 102 also includes a power source 126 (See FIG. 1). The power source 126 is coupled to the motor 406 through a switch (not shown) that is controlled by the electronic controller 122. The switch may be an electromechanical relay or solid-state switch. The power source 126 is configured to provide electrical power to the motor 406 which is then utilized for providing rotational movement to the transmission gear 408 which in turn operates the belt 306 of the chastity device 102. The power source 126 can provide an Alternating Current (AC) or a Direct Current (DC) as per the configuration of the motor 406. In another configuration, the power source 126 may be a battery (e.g., a Lithium-ion battery, Lithium-polymer battery, Nickel-Metal-Hydride battery, etc.) to drive the motor 406.

In an embodiment, when a State of Charge (SoC) of the battery is dropped by a pre-specified value, the sensing module (134) generates an input signal. The input signal generated by the sensing module (134) is sent to the electronic controller 122. Further, the electronic controller 122 first generates the report signal and then transmits the report signal to the monitor client device 108, indicative of drop in the State of Charge (SoC) of the battery by the pre-specified value. For example, when the State of Charge (SoC) of the battery is dropped by 95%, the information is accessed by the monitor 106 using the monitor client device 108.

The electronic controller 122 controls the power supply to the motor 406 through the switch. By regulating the power supply to the motor 406, the rotational speed of the motor 406 may be consequently regulated. For example, the electronic controller 122 regulates a voltage or a current supplied to the motor 406, which in turn regulates the rotational speed of the motor 406. Furthermore, the chastity device 102 may include a clock unit 128 (See FIG. 1), such as a quartz crystal oscillator or a piezoelectric crystal oscillator. The clock unit 128 includes time information related to the operating time of the chastity device 102.

Methods for controlling and monitoring the chastity device 102 may be elucidated using the aforementioned network environment 100 and the construction of the chastity device 102. However, a person skilled in the art would appreciate that the methods that will now be discussed in the following discussion are not limited to the specific configuration of the environment 100 or the specific construction of the chastity device 102 discussed above and may be applied to several alternate configurations and constructions without departing from the scope of the disclosure.

FIG. 5 is a flow diagram illustrating a method 500 for monitoring and controlling the chastity device 102, in accordance with an embodiment of the present disclosure. The method begins at Step 502. At Step 502, the electronic controller 122 generates a report signal indicative of a change in the wearing state of the chastity device 102. Further, the report signal is generated by the electronic controller 122 in response to an input signal received from a peripheral device installed with the chastity device 102. The peripheral device may include the input devices 130 such as the first lock switch 314 and the second lock switch 316. For example, on actuation of the first lock switch 314, the belt 306 may be disengaged and the input signal indicating the disengagement of the belt 306 may be received at the electronic controller 122. Similarly, on actuation of the second lock switch 316, the urination opening port 318 may be opened at the input signal received at the electronic controller 122 may be indicative of the opening of the urination opening port 318.

The peripheral device may also include the communication interface 132. The communication interface 132 may receive the control signal from the monitor client device 108 for change in the wearing state (such as tightening or loosening) of the chastity device 102. The receipt of the control signal at the communication interface 132 may then generate the input signal that is received by the electronic controller 122. In several embodiments of the invention, the control signal may be received from a wearer client device 105 associated with the wearer 104 (See FIG. 1). The wearer client device 105 may be a smartphone, a tablet, a desktop PC, or the like. In that regard, the wearer client device 105 may be authorized to generate the control signal on receipt of an authorization signal from the monitor client device 108.

Further, the peripheral device may also include the sensing module 134. The sensing module 134 in that regard may identify tightening, loosening, or rupture of the belt 306 and generate the input signal that is then received at the electronic controller 122. In several embodiments of the invention, the sensing module 134 may generate the input signal on sensing interruption in current flow in the internal circuitry of the chastity device 102. The interruption in current flow may be determined through a sudden drop in voltage sensed by the voltage sensor of the sensing module 134. In several alternate embodiments of the disclosure, the sensing module 134 may generate the input signal in response to the physiological characteristics of the wearer 104. In one example, when the penis 302 of the wearer 104 undergoes erection due to one or more acts (e.g., due to the sexual activity), the sensing module 134 (e.g., a displacement sensor) detects an increase in size of the penis 302, and accordingly the sensing module 134 generates the input signal indicative of an attempt of sexual activity of the wearer 104. In another example, when swelling of the penis 302 takes place due to one or more incidents (e.g., due to an injury), the sensing module 134 (e.g., strain sensor) detects the swelling of the penis 302, and accordingly the sensing module 134 generates the input signal indicative of the injury of the penis 302 of the wearer 104. In yet another example, the belt 306 may need to be tightened or loosened based on the size of the genitals of the wearer 104, when the chastity device 102 is being changed from one wearer to another wearer. In other instances, the chastity device 102 may need to be unlocked due to a medical emergency, such as after an injury to the area near the genitals of the wearer 104 or if the wearer 104 is suffering from an ailment, etc.

In several alternate embodiments of the present invention, on receipt of the control signal at the communication interface 132, the sensing module 134 may determine the tension in the belt 306. The sensing module 134 may then transmit tension information to the electronic controller 122 as a part of the input signal. Other scenarios where the input signal may be generated and received at the electronic controller 122 may include the opening of a key storage where a key to the chastity device 102 is stored or when the chastity device 102 slips off from the groin area of the wearer 102.

At Step 504, the electronic controller 122 operates the hardware module 402 to change the wearing state of the chastity device 102 in response to the input signal received from the peripheral device. For example, the electronic controller 122 may control the tension in the belt 306 through the motor 406 and the transmission gear 408 to unlock the chastity device 102. As a consequence, the hardware module 402 undergoes transformation from an initial first state to a resultant second state. In several embodiments of the invention, the input signal may include reported operating parameters of the hardware module 402. Therefore, before operating the hardware module 402, the electronic controller 122 may determine whether the reported operating parameters of the hardware module 402 match the preset operating parameters of the hardware module 402. For example, the reported operating parameters may include one of a power parameter and a time parameter. For example, the chastity device 102 may be unlocked by the electronic controller 122 if power available in the power source 126 of the chastity device 102 has dropped below a predetermined threshold value. In another example, the electronic controller 122 may unlock the chastity device 102 if a predetermined period has elapsed since the chastity device 102 was last engaged.

In several alternate embodiments of the disclosure, the reported operating parameters of the hardware module 402 may include communication network parameters. The communication network parameters may be obtained through the communication interface 132 (see FIG. 1) acting as the peripheral device. For example, the electronic controller 122 may unlock the chastity device 102 when the chastity device 102 connects to a wired or wireless network. For example, the electronic controller 122 may be programmed to unlock the chastity device 102 when connecting to a wireless network (e.g., Wi-Fi) having a predefined Service Set Identifier (SSID). In another example, the electronic controller 122 may be programmed to unlock the chastity device 102 when the wearer 104 or the chastity device 102 enters a Geofence defined through a mobile communication network such as GPRS or CDMA. However, the electronic controller 122 may further be programmed to relock the chastity device 102 when the chastity device 102 disconnects from the particular wired or wireless network.

In several embodiments of the invention, the reported operating parameters include information associated with a second hardware module (not shown) of a second chastity device 140 (See FIG. 1) connected to the network 110. In several embodiments, the second chastity device 140 is a virginity device. Further, a second wearer device 137 is associated with the second chastity device 140. In that regard, the electronic controller 122 may unlock the chastity device 102, and/or a second electronic controller (not shown) of the second chastity device 140 may unlock the second chastity device 140 when both the first 102 and the second 140 chastity devices satisfy predefined conditions. For example, the predefined conditions may include the first 102 and the second 140 chastity devices being within a predetermined distance of each other, having identical communication network parameters or power parameters or time parameters, or being associated with a common monitor client device, etc. In such a scenario, the peripheral device may generate the input signal indicative of the predefined conditions being satisfied. The input signal is then transmitted to the electronic controller 122. In several embodiments of the invention, the input signal may also be generated immediately following one of the wearer client device 105 and the second wearer client device 137 being connected to the same communication network, such as the network 110, to which the other of the wearer client device 105 and the second wearer client device 137 has already been in connection with. The electronic controller 122 may then operate the hardware module 402 to unlock the chastity device 102 upon matching the preset operating parameters of the hardware module 402 with the reported operating parameters reported by the peripheral device within the input signal.

At Step 506, the electronic controller 122 then transmits the report signal to the monitor client device 108 associated with the monitor 106, through the communication interface 132 and the network 110. In that regard, the report signal reports the unlocking of the chastity device 102 to the monitor client device 108. In several embodiments of the disclosure, the change in the wearing state of the chastity device 102 includes the locking or the unlocking of the chastity device 102 in response to the control signal received from the monitor client device 108. Therefore, the report signal reports the locking or the unlocking to the monitor client device 108.

At Step 508, the electronic controller 122 transmits an electronic message to the monitor client device 108. The electronic message is indicative of at least the current wearing state of the chastity device 102. The electronic message being received by the monitor client device 108 may include at least one of an audio file, an image file, or a video file. These forms of electronic messages are indicative of at least the current wearing state of the chastity device 102 or the change in the wearing status over a period of time. For example, the monitor client device 108 may receive the electronic message at a first pre-specified time instance, a second pre-specified time instance, and a third pre-specified time instance in the form of images, audios, videos, etc. depicting the wearing status of the chastity device 102. Time intervals between the first pre-specified time instance, the second pre-specified time instance, and the third pre-specified time instance may be pre-defined by the monitor 106 and can be adjusted as per the need of the monitor 106. In several embodiments of the invention, the electronic message may include a wearing state change time instance information, the wearing state of the chastity device 102 before and after the instance of the wearing state change, the mode of change of the wearing state, etc. In several embodiments of the invention, the electronic controller 122 may directly transmit the electronic message to the monitor client device 108 through the network 110. In several alternate embodiments, the electronic controller 122 may transmit the electronic message to the wearer client device 105, and the wearer client device 105 may then forward the electronic message to the monitor client device 108 through the network 110. In addition, the electronic controller 122 may also transmit the electronic message to the storage module 136 where the electronic message may be recorded for future use.

Embodiments of the present invention as described above offer several advantages. For instance, the chastity device may be operated remotely by the monitor using the monitor client device. Further, in case of an emergency, the chastity device may be automatically unlocked without the intervention of the monitor. Furthermore, the monitor may, in some instances, authorize the wearer to unlock the chastity device themselves during the emergency. Moreover, relaxations may be provided to the wearer wherever there are situations like low battery power, elapsing of preset time interval or wearer being present in certain network/geographical locations. However, in either of the cases, after every event of locking or unlocking and even at other times, the monitor is kept abreast with the progress of the wearer and different states of the chastity device during the monitoring period.

Various embodiments of the disclosure, as discussed above, may be practiced with steps and/or operations in a different order, and/or with hardware elements in configurations, which are different from those which are disclosed. Therefore, although the disclosure has been described based on these exemplary embodiments, it is noted that certain modifications, variations, and alternative constructions may be apparent and well within the scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

The invention claimed is:

1. A method of monitoring and controlling a chastity device, the method comprising:
   generating, by an electronic controller, a report signal indicative of a change in a wearing state of the chastity device;
   transmitting, by the electronic controller, the report signal to a monitor client device associated with a monitor, the report signal being generated by the electronic controller in response to an input signal received from a peripheral device associated with the chastity device;
   determining, by a sensing module of the peripheral device, a tension in a belt of the chastity device; and
   transmitting, by the sensing module, tension information to the electronic controller as a part of the input signal, wherein the report signal reports the tension information to the monitor client device.

2. The method as claimed in claim 1, further comprising operating, by the electronic controller, a hardware module to change the wearing state of the chastity device in response to the input signal received from the peripheral device.

3. The method as claimed in claim 2, wherein the monitor client device is communicably coupled to the hardware module and is adapted to provide a control signal to the electronic controller for controlling a change in the wearing state of the chastity device.

4. The method as claimed in claim 2, wherein the hardware module comprises a first lock switch and a second lock switch, the first lock switch being configured to control the wearing state of the chastity device, and the second lock switch being configured to control a urination port opening of the chastity device.

5. The method as claimed in claim 2, wherein a wearer client device associated with a wearer of the chastity device is communicably coupled to the hardware module and is authorized to provide a control signal to the electronic controller for controlling a change in the wearing state of the chastity device, after receiving an authorization signal from the monitor client device.

6. The method as claimed in claim 1, further comprising:
   determining, by the electronic controller, whether preset operating parameters of the hardware module match reported operating parameters reported by the peripheral device, the reported operated parameters being included in the input signal; and
   operating, by the electronic controller, the hardware module upon matching the preset operating parameters of the hardware module with the reported operating parameters reported by the peripheral device.

7. The method as claimed in claim 6, wherein the reported operating parameters comprise one of a power parameter and a time parameter.

8. The method as claimed in claim 6, wherein:
   the reported operating parameters comprise communication network parameters, and
   the peripheral device is a communication interface.

9. The method as claimed in claim 6, wherein the reported operating parameters comprise information associated with a second hardware module of a second chastity device.

10. The method as claimed in claim 1, wherein the peripheral device is selected from a group comprising input devices, a communication interface, and the sensing module.

11. The method as claimed in claim 10, further comprising generating, by the sensing module, the input signal in response to physiological characteristics of a wearer of the chastity device.

12. The method as claimed in claim 1, further comprising transmitting, by the electronic controller, an electronic message to the monitor client device, the electronic message indicating at least a current wearing state of the chastity device.

13. The method as claimed in claim 12, further comprising transmitting, by the electronic controller, the electronic message to a storage module and a wearer client device associated with the wearer,
   wherein the storage module records the electronic message.

14. The method as claimed in claim 1, wherein the change in the wearing state of the chastity device includes locking or unlocking of the chastity device in response to a control signal received from the monitor client device or a wearer client device, the report signal reporting the locking or the unlocking to the monitor client device.

15. A non-transitory computer readable medium having a program stored thereon, the program being executable by an electronic controller of a chastity device to control the electronic controller to perform operations comprising:

generating a report signal indicative of a change in a wearing state of the chastity device;

transmitting the report signal to a monitor client device associated with a monitor, the report signal being generated by the electronic controller in response to an input signal received from a peripheral device associated with the chastity device;

determining, by a sensing module of the peripheral device, a tension in a belt of the chastity device; and transmitting, by the sensing module, tension information to the electronic controller as a part of the input signal, wherein the report signal reports the tension information to the monitor client device.

* * * * *